United States Patent [19]
Kong et al.

[11] Patent Number: 6,048,719
[45] Date of Patent: Apr. 11, 2000

[54] METHOD FOR CLONING AND PRODUCING THE DRAIII RESTRICTION ENDONUCLEASE

[75] Inventors: Huimin Kong, Wenham; Lauren S. Higgins, Essex; Michael A. Dalton, Manchester, all of Mass.

[73] Assignee: New England Biolabs, Inc., Beverly, Mass.

[21] Appl. No.: 09/235,246

[22] Filed: Jan. 22, 1999

[51] Int. Cl.[7] .............................. C12N 9/22; C12N 15/55
[52] U.S. Cl. ................. 435/199; 435/252.3; 435/252.33; 435/320.1; 435/478; 536/23.2
[58] Field of Search .................................. 435/199, 320.1, 435/252.3, 252.33, 478; 536/23.2

[56] References Cited

U.S. PATENT DOCUMENTS

| | | | |
|---|---|---|---|
| 4,863,858 | 9/1989 | Grosskopf | 435/91 |
| 5,200,333 | 4/1993 | Wilson | 435/172.3 |
| 5,320,957 | 6/1994 | Brooks et al. | 435/172.3 |
| 5,492,823 | 2/1996 | Xu et al. | 435/199 |

OTHER PUBLICATIONS

Roberts et al, Nucl. Acids Res. 26:338–350 (1998).
Kosykh et al., Mol. Gen. Genet. 178:717–719 (1980).
Mann et al., Gene 3:97–112 (1978).
Walder et al., Proc. Nat. Acad. Sci. 78:1503–1507 (1981).
Bouqueleret et al., Nucl. Acids Res. 12:3659–3676 (1984).
Gingeras et al., Proc. Natl. Acad. Sci. USA 80:402–406 (1983).
Theriault et al., Gene 19:355–359 (1982).
Blumenthal et al., J. Bacteriol. 164:501–509 (1985).
Looney, et al., Gene, 80:193–208 (1989).
Kiss et al., Nucl. Acids. Res. 13:6403–6421 (1985).
Szomolanyi et al., Gene 10:219–225 (1980).
Janulaitis et al., Gene 20:197–204 (1982).
Kiss et al., Gene 21:111–119 (1983).
Walder et al., J. Biol. Chem. 258:1235–1241 (1983).
Fomenkov et al., Nucl. Acids Res. 22:2399–2403 (1994).
Piekarowicz, et al., Nucl. Acids Res., 19:1831–1835 (1991).
Piekarowicz, et al., J. Bacteriology 173:150–155 (1991).
Lunnen, et al., Gene 74:25–32 (1988).
Raleigh & Wilson, Proc. Natl. Acad. Sci. USA, 83:9070–9074 (1986).
Heitman and Model, J. Bacteriology, 169:3243–3250 (1987).
Raleigh, et al., Genetics, 122–279–296 (1989).
Waite–Rees, et al., J. Bacteriology, 173:5207–5219 (1991).
Ochman, et al., Genetics, 120:621 (1988).
Triglia, Nucl. Acids Res., 16:8186 (1988).
Silver and Keerikatte, J. Cell. Biochem (Suppl.) 13E:306 Abstract No. WH239 (1989).
Ives, et al., J. Bacteriology, 177:6313 (1995).
Matsudaira, J. Biol. Chem., 262:10035–10038 (1987).

*Primary Examiner*—Charles L. Patterson, Jr.
*Attorney, Agent, or Firm*—Gregory D. Williams

[57] ABSTRACT

The present invention relates to the recombinant DNA which encodes the DraIII restriction endonuclease modification methylase, and the production of DraIII restriction endonuclease from the recombinant DNA. Related expression vectors, pHKUV5 vector which features a strong, constitutive UV5 promoter without the Lac repressor binding site and pHKT7 vector which contains a powerful controllable T7 promoter and a low copy number origin of replication, are also disclosed.

6 Claims, 10 Drawing Sheets

FIG. 3

```
         10                  30                  50
ATGGAATTGTGCCATAAAACTGTCAAGTCAAGAACCGCCTACTCCAAACATTTTCCTCAC
MetGluLeuCysHisLysThrValLysSerArgThrAlaTyrSerLysHisPheProHis 70                  90                 110
AAATGTCAGCTTCCTTTAGGTCATAGTGGCAAATGTCTCGAATTTCCTTTTTTAGTCAGC
LysCysGlnLeuProLeuGlyHisSerGlyLysCysLeuGluPheProPheLeuValSer 130                 150                 170
CTTTCAAAAACGCATCCTCGAATCGCAGCTAAGATTGTTCGAGATGCAACTATGACTACA
LeuSerLysThrHisProArgIleAlaAlaLysIleValArgAspAlaThrMetThrThr 190                 210                 230
GGGGCAGCTTGGAAGAGTTCACAGGCTGGGCCTAATAGAATGCCAAGGTATGTTGCAATA
GlyAlaAlaTrpLysSerSerGlnAlaGlyProAsnArgMetProArgTyrValAlaIle 250                 270                 290
CTTGACGATGATATTCTACTGGAGAAATTCAACCTTGATATGCAGTCCCTACCCGAGATT
LeuAspAspAspIleLeuLeuGluLysPheAsnLeuAspMetGlnSerLeuProGluIle 310                 330                 350
ACTAGATTGAAAATTAGGGAAAAGGCCGCAGATTATGATTCATGTATAGATGTAGCCAGA
ThrArgLeuLysIleArgGluLysAlaAlaAspTyrAspSerCysIleAspValAlaArg 370                 390                 410
AAGTTAACTTGGCTAGCCTATCAATTGCACGGTGCGCCAATACCCGATAGTTTCACAAAG
LysLeuThrTrpLeuAlaTyrGlnLeuHisGlyAlaProIleProAspSerPheThrLys 430                 450                 470
AATTATTTAGAAGAATTCTTTGGGCCAATGGTGGCGGGGTCTACAAATTGTGAGATTTGC
AsnTyrLeuGluGluPhePheGlyProMetValAlaGlySerThrAsnCysGluIleCys 490                 510                 530
AAGCTCCCTCTAACCATTGACCTATTTTCCGAAAATAGGGTAGGTAAGGCTGCCGTGGAA
LysLeuProLeuThrIleAspLeuPheSerGluAsnArgValGlyLysAlaAlaValGlu 550                 570                 590
ACTGCCCACAAGACACCCAGATTACATAATGCCGAGAATGTAGGATTTGCCCATAGGTTT
ThrAlaHisLysThrProArgLeuHisAsnAlaGluAsnValGlyPheAlaHisArgPhe 610                 630                 650
TGCAATGTGGCACAGGGGAATAAATCACTAGACGAATTTTATCTGTGGATGGAAGAGGTT
CysAsnValAlaGlnGlyAsnLysSerLeuAspGluPheTyrLeuTrpMetGluGluVal

670
TTGACTCGCGTAAAAAATGCTATAG
LeuThrArgValLysMetLeuEnd
```

FIG. 4A

```
         10                    30                    50
ATGACGAATGTGGAACAAGTTGTTGCCGATTACCCAAGGAGATTTAAGAACCTTTACTAC
MetThrAsnValGluGlnValValAlaAspTyrProArgArgPheLysAsnLeuTyrTyr 70                    90                   110
AGACTTTACACAAATAGTAATTCTAGTCGCGCCGAGAAACTAATTTACGAATTGTCGCGA
ArgLeuTyrThrAsnSerAsnSerSerArgAlaGluLysLeuIleTyrGluLeuSerArg 130                   150                   170
ATACTTTTGCTTAAATTGGCGGCGGAGAGGCGAAATGGAAAAACGGTTTTAAGTAACTTT
IleLeuLeuLeuLysLeuAlaAlaGluArgArgAsnGlyLysThrValLeuSerAsnPhe 190                   210                   230
ATCGATGATCCAGTCAATAATCAAGAAGACCTGCTTAAGTTGGGTGGAGATGAATTTGAA
IleAspAspProValAsnAsnGlnGluAspLeuLeuLysLeuGlyGlyAspGluPheGlu 250                   270                   290
ATATTGGAAAATCAAGATAAATATTTTTCGCTTGATCTGTCTTCGGTTGTTTCGGCATTT
IleLeuGluAsnGlnAspLysTyrPheSerLeuAspLeuSerSerValValSerAlaPhe 310                   330                   350
GCGGAGATATCCGATATTGAACTTCATAGTGCCCCTGGACATATTGTTGGAGATGCCTTT
AlaGluIleSerAspIleGluLeuHisSerAlaProGlyHisIleValGlyAspAlaPhe 370                   390                   410
CAGGCTTTGATAGGGCCAACTATTCGCGGAGATAAAGGGCAGTTTTTCACACCTAAGAAT
GlnAlaLeuIleGlyProThrIleArgGlyAspLysGlyGlnPhePheThrProLysAsn 430                   450                   470
TTAACGGATGCGATAATAAAGATTTTATCCCCTAAGCCTGGAGACAAAATTATTGATCCT
LeuThrAspAlaIleIleLysIleLeuSerProLysProGlyAspLysIleIleAspPro 490                   510                   530
GCCTGTGGAACGGGAGGATTTCTTTCTTCATGTCAAGCATATTGGGAATTGACATATAAA
AlaCysGlyThrGlyGlyPheLeuSerSerCysGlnAlaTyrTrpGluLeuThrTyrLys 550                   570                   590
GATCCTACTGCTCGCTATGAAATCTTAGGTATTGATAAAGACGCCGATATGGCCATGCTA
AspProThrAlaArgTyrGluIleLeuGlyIleAspLysAspAlaAspMetAlaMetLeu 610                   630                   650
TCTAGTGCGTTGCTAGAAATTTCAACCAACGGATTTGCTAAGGTGGTAAAACTCAGACTCA
SerSerAlaLeuLeuGluIleSerThrAsnGlyPheAlaLysValValAsnSerAspSer 670                   690                   710
TTAAAATTTATTATTGACAATCCTCAATACGAAGAACAGTTTGATATAGTTGTGGCAAAT
LeuLysPheIleIleAspAsnProGlnTyrGluGluGlnPheAspIleValValAlaAsn
```

FIG. 4B

```
          730               750               770
CCGCCGTTTGGTACGAAAATTAAAGTAGATAATAAGGCTATACTAAAAGATTACCAACTC
ProProPheGlyThrLysIleLysValAspAsnLysAlaIleLeuLysAspTyrGlnLeu 790               810               830
GGTCACTCATGGAAAGTGGAAAAATGGTACTCTATGTCCAAGCAGACACATTCTTGGTGCG
GlyHisSerTrpLysValGluAsnGlyThrLeuCysProSerArgHisIleLeuGlyAla 850               870               890
CAAGACCCACAAATTCTTTTTATAGAGTTGTGCGTGAAGCTTCTCAAGGAAAATGGTAGG
GlnAspProGlnIleLeuPheIleGluLeuCysValLysLeuLeuLysGluAsnGlyArg 910               930               950
ATGGCTCTTATATTACCGGAGGGAGTGTTCGGTGGGAAGTCATCAGAATATGTGTGGGAA
MetAlaLeuIleLeuProGluGlyValPheGlyGlyLysSerSerGluTyrValTrpGlu 970               990              1010
TATCTGAAAAATAGAGGTATAGTTTTTGCCTTAATTGATTGTCCGCGAACAACTTTCCAG
TyrLeuLysAsnArgGlyIleValPheAlaLeuIleAspCysProArgThrThrPheGln 1030              1050              1070
CCATACACGGATATTAAAACTAATGTGCTTTTCTTCAAAAAAACGAAAGAAATGCCGGAA
ProTyrThrAspIleLysThrAsnValLeuPhePheLysLysThrLysGluMetProGlu 1090              1110              1130
GAAAAAACGCAGGTAGCTGTAGCTAAAAGGTGCGGTCATGATAAGCGCGGCCGCACTCAC
GluLysThrGlnValAlaValAlaLysArgCysGlyHisAspLysArgGlyArgThrHis 1150              1170              1190
TACCCTTCAGGACTCTCCGTTCCAGATGATTTTGCGGATATAGCAAATCTATTTNATGAG
TyrProSerGlyLeuSerValProAspAspPheAlaAspIleAlaAsnLeuPheXxxGlu 1210              1230              1250
GGTATAGAAAACAGGATCTGGAAATCTGTCTGTTTGAAAAAGGAATATAGAGTCCCAAGA
GlyIleGluAsnArgIleTrpLysSerValCysLeuLysLysGluTyrArgValProArg 1270              1290              1310
TATTATTTCAATGATGATGAAGCAGGCAAATTGGACAACATAGGTCAAGTTATAACCATT
TyrTyrPheAsnAspAspGluAlaGlyLysLeuAspAsnIleGlyGlnValIleThrIle 1330              1350              1370
GGTGAGTTAATTAGAATGGGAGTTTTGAAAATAAGAAAAGGTCACGAAGTTGGCTCAGAA
GlyGluLeuIleArgMetGlyValLeuLysIleArgLysGlyHisGluValGlySerGlu 1390              1410              1430
AACTATGGTACGGGTGATATTCCGTTCATAAGAACCTCCGACATAAATAATTTGGAGTTT
AsnTyrGlyThrGlyAspIleProPheIleArgThrSerAspIleAsnAsnLeuGluPhe 1450              1470              1490
TCTTCCGATCCCACAAATTCTGTCAGCGAAGAAATATATGAAATGTATTCGAAAAAACAG
SerSerAspProThrAsnSerValSerGluGluIleTyrGluMetTyrSerLysLysGln
```

FIG. 4C

```
         1510              1530              1550
AATATCGCCGCCGGGGACATATTAATGGCAGTAGATGGGAGATACAGAATTGGAAAAACC
AsnIleAlaAlaGlyAspIleLeuMetAlaValAspGlyArgTyrArgIleGlyLysThr 1570              1590              1610
GCTNTGGTCACCGAAGAGAATTCGAGGTGCATAGTACAAAGTCATATAAAAATATTATCA
AlaXxxValThrGluGluAsnSerArgCysIleValGlnSerHisIleLysIleLeuSer 1630              1650              1670
GTAGAATTTAACAGTTTAATAAATAACTATGAATTATTATATATGTTAAATTTGGCCGAA
ValGluPheAsnSerLeuIleAsnAsnTyrGluLeuLeuTyrMetLeuAsnLeuAlaGlu 1690              1710              1730
GTGCAGAATCAAGTTCGGAATATGGTTTTTGTTCAATCAACACTTGGTACTCTAGGCAAT
ValGlnAsnGlnValArgAsnMetValPheValGlnSerThrLeuGlyThrLeuGlyAsn 1750              1770              1790
AGGTTAGAGCAGGTAAAGATTGCAATACCTCGACGCAATAGCGAATGGGATAAAATGATA
ArgLeuGluGlnValLysIleAlaIleProArgArgAsnSerGluTrpAspLysMetIle 1810              1830              1850
GCCGGATTTAAGCATATTTTGGAAGAGAGGAGTAGACTGCTGGTATCTATACGCGGACTG
AlaGlyPheLysHisIleLeuGluGluArgSerArgLeuLeuValSerIleArgGlyLeu

1870
GCACATGAAGCAGAGCTATAG
AlaHisGluAlaGluLeuEnd
```

FIG. 5

```
        10                      30                      50
ATGAGTGATTCGGGCGCTATTGCTATAGGTTTCGCAATTAAGCGGCTTAGAAGCTCCAAG
MetSerAspSerGlyAlaIleAlaIleGlyPheAlaIleLysArgLeuArgSerSerLys 70                      90                     110
AAGCTATCTCAAGAGAGCTTGGCAGAAATGTCTGGTATTCACCGCACTTATATCAGTTCA
LysLeuSerGlnGluSerLeuAlaGluMetSerGlyIleHisArgThrTyrIleSerSer 130                     150                     170
ATAGAGCGCGGAGAGCGAAACGTCGGGATAAACATGCTTCTATCTATTCTTGACGCATTG
IleGluArgGlyGluArgAsnValGlyIleAsnMetLeuLeuSerIleLeuAspAlaLeu 190                     210                     230
GAACAGAAACCCTCCAGCTTCTTTAGGGAGCTGGAAGACGAGGGGGTATTTTAA
GluGlnLysProSerSerPhePheArgGluLeuGluAspGluGlyValPheEnd
```

FIG. 7A

```
   1  GACGAAAGGG CCTCGTGATA CGCCTATTTT TATAGGTTAA TGTCATGATA
  51  ATAATGGTTT CTTAGACGTC AGGTGGCACT TTTCGGGGAA ATGTGCGCGG
 101  AACCCCTATT TGTTTATTTT TCTAAATACA TTCAAATATG TATCCGCTCA
 151  TGAGACAATA ACCCTGATAA ATGCTTCAAT AATATTGAAA AAGGAAGAGT
 201  ATGAGTATTC AACATTTCCG TGTCGCCCTT ATTCCCTTTT TTGCGGCATT
 251  TTGCCTTCCT GTTTTTGCTC ACCCAGAAAC GCTGGTGAAA GTAAAAGATG
 301  CTGAAGATCA GTTGGGTGCA CGAGTGGGTT ACATCGAACT GGATCTCAAC
 351  AGCGGTAAGA TCCTTGAGAG TTTTCGCCCC GAAGAACGTT TTCCAATGAT
 401  GAGCACTTTT AAAGTTCTGC TATGTGGCGC GGTATTATCC CGTATTGACG
 451  CCGGGCAAGA GCAACTCGGT CGCCGCATAC ACTATTCTCA GAATGACTTG
 501  GTTGAGTACT CACCAGTCAC AGAAAAGCAT CTTACGGATG GCATGACAGT
 551  AAGAGAATTA TGCAGTGCTG CCATAACCAT GAGTGATAAC ACTGCGGCCA
 601  ACTTACTTCT GACAACGATC GGAGGACCGA AGGAGCTAAC CGCTTTTTTG
 651  CACAACATGG GGGATCATGT AACTCGCCTT GATCGTTGGG AACCGGAGCT
 701  GAATGAAGCC ATACCAAACG ACGAGCGTGA CACCACGATG CCTGTAGCAA
 751  TGGCAACAAC GTTGCGCAAA CTATTAACTG GCGAACTACT TACTCTAGCT
 801  TCCCGGCAAC AATTAATAGA CTGGATGGAG GCGGATAAAG TTGCAGGACC
 851  ACTTCTGCGC TCGGCCCTTC CGGCTGGCTG GTTTATTGCT GATAAATCTG
 901  GAGCCGGTGA GCGTGGGTCT CGCGGTATCA TTGCAGCACT GGGGCCAGAT
 951  GGTAAGCCCT CCCGTATCGT AGTTATCTAC ACGACGGGGA GTCAGGCAAC
1001  TATGGATGAA CGAAATAGAC AGATCGCTGA GATAGGTGCC TCACTGATTA
1051  AGCATTGGTA ACTGTCAGAC CAAGTTTACT CATATATACT TTAGATTGAT
1101  TTAAAACTTC ATTTTTAATT TAAAAGGATC TAGGTGAAGA TCCTTTTTGA
1151  TAATCTCATG ACCAAAATCC CTTAACGTGA GTTTTCGTTC CACTGAGCGT
1201  CAGACCCCGT AGAAAAGATC AAAGGATCTT CTTGAGATCC TTTTTTTCTG
1251  CGCGTAATCT GCTGCTTGCA AACAAAAAAA CCACCGCTAC CAGCGGTGGT
```

FIG. 7B

```
1301 TTGTTTGCCG GATCAAGAGC TACCAACTCT TTTTCCGAAG GTAACTGGCT
1351 TCAGCAGAGC GCAGATACCA AATACTGTCC TTCTAGTGTA GCCGTAGTTA
1401 GGCCACCACT TCAAGAACTC TGTAGCACCG CCTACATACC TCGCTCTGCT
1451 AATCCTGTTA CCAGTGGCTG CTGCCAGTGG CGATAAGTCG TGTCTTACCG
1501 GGTTGGACTC AAGACGATAG TTACCGGATA AGGCGCAGCG GTCGGGCTGA
1551 ACGGGGGGTT CGTGCACACA GCCCAGCTTG GAGCGAACGA CCTACACCGA
1601 ACTGAGATAC CTACAGCGTG AGCTATGAGA AAGCGCCACG CTTCCCGAAG
1651 GGAGAAAGGC GGACAGGTAT CCGGTAAGCG GCAGGGTCGG AACAGGAGAG
1701 CGCACGAGGG AGCTTCCAGG GGGAAACGCC TGGTATCTTT ATAGTCCTGT
1751 CGGGTTTCGC CACCTCTGAC TTGAGCGTCG ATTTTTGTGA TGCTCGTCAG
1801 GGGGGCGGAG CCTATGGAAA AACGCCAGCA ACGCGGCCTT TTTACGGTTC
1851 CTGGCCTTTT GCTGGCCTTT TGCTCACATG GCGCTCACTG CCCGCTTTCC
1901 AGTCGGGAAA CCTGTCGTGC CAGCTGCATT AATGAATCGG CCAACGCGCG
1951 GGGAGAGGCG GTTTGCGTAT TGGGCGCCAG GGTGGTTTTT CTTTTCACCA
2001 GTGAGACGGG CAACAGCTGA TTGCCCTTCA CCGCCTGGCC CTGAGAGAGT
2051 TGCAGCAAGC GGTCCACGCT GGTTTGCCCC AGCAGGCGAA AATCCTGTTT
2101 GATGGTGGTT AACGGCGGGA TATAACATGA GCTGTCTTCG GTATCGTCGT
2151 ATCCCACTAC CGAGATATCC GCACCAACGC GCAGCCCGGA CTCGGTAATG
2201 GCGCGCATTG CGCCCAGCGC CATCTGATCG TTGGCAACCA GCATCGCAGT
2251 GGGAACGATG CCCTCATTCA GCATTTGCAT GGTTTGTTGA AAACCGGACA
2301 TGGCACTCCA GTCGCCTTCC CGTTCCGCTA TCGGCTGAAT TTGATTGCGA
2351 GTGAGATATT TATGCCAGCC AGCCAGACGC AGACGCGCCG AGACAGAACT
2401 TAATGGGCCC GCTAACAGCG CGATTTGCTG GTGACCCAAT GCGACCAGAT
2451 GCTCCACGCC CAGTCGCGTA CCGTCTTCAT GGGAGAAAAT AATACTGTTG
2501 ATGGGTGTCT GGTCAGAGAC ATCAAGAAAT AACGCCGGAA CATTAGTGCA
2551 GGCAGCTTCC ACAGCAATGG CATCCTGGTC ATCCAGCGGA TAGTTAATGA
2601 TCAGCCCACT GACGCGTTGC GCGAGAAGAT TGTGCACCGC CGCTTTACAG
```

FIG. 7C

```
2651 GCTTCGACGC CGCTTCGTTC TACCATCGAC ACCACCACGC TGGCACCCAG

2701 TTGATCGGCG CGAGATTTAA TCGCCGCGAC AATTTGCGAC GGCGCGTGCA

2751 GGGCCAGACT GGAGGTGGCA ACGCCAATCA GCAACGACTG TTTGCCCGCC

2801 AGTTGTTGTG CCACGCGGTT GGGAATGTAA TTCAGCTCCG CCATCGCCGC

2851 TTCCACTTTT TCCCGCGTTT TCGCAGAAAC GTGGCTGGCC TGGTTCACCA

2901 CGCGGGAAAC GGTCTGATAA GAGACACCGG CATACTCTGC GACATCGTAT

2951 AACGTTACTG GTTTCACATT CACCACCCTG AATTGACTCT CTTCCGGGCG

3001 CTATCATGCC ATACCGCGAA AGGTTTTGCG CCATTCGATG GTGTCAGCGT

3051 GAGTTAGCTC ACTCATTAGG CACCCCAGGC TTTACACTTT ATGCTTCCGG

3101 CTCGTATAAT GTGTGGAATC ACACAGGAAA CAGCTATGAC CATGATTACG
                                                    -10
3151 CCAAGCTTGC ATGCCTGCAG GTCGACTCTA GAGGATCCCC GGGTACCGAG
         HindIII
3201 CTCGAATTCA CTGGCCGTCG TTTTACAACG TCGTGACTGG GAAAACCCTG
        EcoRI
3251 GCGTTACCCA ACTTAATCGC CTTGCAGCAC ATCCCCCTTT CGCCAGCTGG

3301 CGTAATAGCG AAGAGGCCCG CACCGATCGC CCTTCCCAAC AGTTGCGCAG

3351 CCTGAATGGC GAATGGCGCC TGATGCGGTA TTTTCTCCTT ACGCATCTGT

3401 GCGGTATTTC ACACCGCATA TGGTGCACTC TCAGTACAAT CTGCTCTGAT

3451 GCCGCATAGT TAAGCCAGCC CCGACACCCG CCAACACCCG CTGACGCGCC

3501 CTGACGGGCT TGTCTGCTCC CGGCATCCGC TTACAGACAA GCTGTGACCG

3551 TCTCCGGGAG CTGCATGTGT CAGAGGTTTT CACCGTCATC ACCGAAACGC

3601 GCGA
```

METHOD FOR CLONING AND PRODUCING THE DRAIII RESTRICTION ENDONUCLEASE

BACKGROUND OF THE INVENTION

The present invention relates to the recombinant DNA which encodes the DraIII restriction endonuclease and modification methylase, and the production of DraIII restriction endonuclease from the recombinant DNA. DraIII restriction endonuclease is originally isolated from *Deinococcus radiophilus*. It recognizes the DNA sequence 5' CACNNNGTG 3' and cleaves the phosphodiester bond 5' to the first G of the recognition sequence to produce a 3 base 3' extension.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Type II restriction endonucleases act by recognizing and binding to particular sequences of nucleotides (the 'recognition sequence') along the DNA molecule. Once bound, they cleave the DNA molecule at specific positions. Different restriction endonucleases have affinity for different recognition sequences. More than 3000 restriction endonucleases have been characterized so far, and they recognize 212 different recognition sequences (Roberts, R. J., Macelis, D. *Nucleic Acids Res.* 26:338–350 (1998)).

It is thought that in nature, restriction endonucleases play a protective role in the welfare of the bacterial cell. They enable bacteria to resist infection by foreign DNA molecules like bacteriophages and plasmids that would otherwise destroy or parasitize them. They impart resistance by cleaving invading foreign DNA molecules each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify the target nucleotide within the sequence by the addition of a methyl group. Following methylation, the recognition sequence is no longer cleaved by the restriction endonuclease. The DNA of a bacterial cell is always modified by virtue of the activity of its modification methylase. It is therefore insensitive to the presence of the endogenous restriction endonuclease. It is only unmodified, and therefore identifiable foreign DNA, that is sensitive to restriction endonuclease recognition and cleavage.

With the advent of genetic engineering technology, it is now possible to clone genes and to produce the proteins that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as 10-3 to 10-4. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178:717–719, (1980); HhaII: Mann et al., *Gene* 3:97–112, (1978); PstI: Walder et al., *Proc. Nat. Acad. Sci.* 78:1503–1507, (1981). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985)).

A third approach which is being used to clone a growing number of systems, involves selection for an active methylase gene (refer to U.S. Pat. No. 5,200,333 and BsuRI: Kiss et al., *Nucl. Acid. Res.* 13:6403–6421, (1985)). Since restriction and modification genes are often closely linked, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al, *Gene* 20:197–204 (1982); BsuRI: Kiss and Baldauf, *Gene* 21:111–119, (1983); and MspI: Walder et al., *J. Biol. Chem.* 258:1235–1241, (1983)).

Another method for cloning methylase and endonuclease genes is based on a colorimetric assay for DNA damage (see, U.S. Pat. No. 5,492,823). When screening for a methylase, the plasmid library is transformed into the host *E. coli* strain such as AP1-200. The expression of a methylase will induce the SOS response in an *E. coli* strain which is McrA+, McrBC+, or Mrr+. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz, et. al., *Nucleic Acids Res.* 19:1831–1835, (1991) and Piekarowicz, et. al. *J. Bacteriology* 173:150–155 (1991)). Likewise, the *E. coli* strain ER1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Xu et. al. *Nucleic Acids Res.* 22:2399–2403 (1994)).

Sometimes the straight-forward methylase selection method fails to yield a methylase (and/or endonuclease) clone due to various obstacles. See, e.g., Lunnen, et al., *Gene,* 74(1):25–32 (1988). One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease (see, U.S. Pat. No. 5,320, 957).

Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci., USA* 83:9070–9074, (1986)) or methylated adenine (Heitman and Model,*J. Bact.* 196:3243–3250, (1987); Raleigh, Trimarchi, and Revel, *Genetics,* 122:279–296, (1989) Waite-Rees, et al., *J. Bacteriology,* 173:5207–5219 (1991)). Cytosine-specific or adenine-specific methylase genes cannot be cloned easily into these strains, either on their own, or together with their corresponding endonuclease genes. To avoid this problem it is necessary to use mutant strains of *E. coli* (McrA- and McrB- or Mrr-) in which these systems are defective.

A third potential difficulty is that some restriction endonuclease and methylase genes may not express in *E. coli* due to differences in the transcription machinery of the source organism and *E. coli,* such as differences in promoter and ribosome binding sites. The methylase selection technique requires that the methylase express well enough in *E. coli* to fully protect at least some of the plasmids carrying the gene.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY OF THE INVENTION

A unique combination of methods was used to directly clone the DraIII endonuclease gene and express the gene in an *E. coli* strain premodified by DraIII methylase. To clone the DraIII endonuclease gene directly, both the N-terminal amino acid sequence and a stretch of internal amino acid sequence of highly purified native DraIII restriction endonuclease were determined. Degenerate primers were designed based on the amino acid sequences and PCR techniques were used to amplify the DNA fragment that encodes the DraIII endonuclease protein. The PCR product was sequenced and the information was used to design primers for inverse PCR reactions. By chromosome walking via inverse PCR, the endonuclease open reading frame, draIIIR, was deduced. Continuing with inverse PCR, open reading frames were found upstream and downstream of the endonuclease gene. Blast analysis suggested that the upstream gene encoded a C protein (control protein, draIIIC) and the downstream gene encoded an adenine methylase (draIIIM).

A new expression vector, pHKUV5, was specially engineered to express DraIII methylase, because the expression levels of DraIII methylase in *E. coli* host is extremely low. DraIII endonuclease gene was cloned into a low copy-number T7 expression vector, pHKT7, and transformed into the *E. coli* host which was premodified by DraIII methylase cloned in pHKUV5. This recombinant *E. coli* strain (NEB#1176) produces about 1.6×10^6 units DraIII endonuclease per gram cell. The yield of recombinant DraIII endonuclease is 500-fold higher than the yield of native endonuclease from *Deinococcus radiophilus.*

BRIEF DESCRIPTION OF THE DRAWINGS

FIG. 3 shows the DNA sequence of draIIIR gene and its encoded amino acid sequence (SEQ ID NO:1).

FIG. 4 shows the DNA sequence of draIIIM gene and its encoded amino acid sequence (SEQ ID NO:2).

FIG. 5 shows the DNA sequence of draIIIC gene and its encoded amino acid sequence (SEQ ID NO:3).

FIG. 7 shows the DNA sequence of pHKUV5 plasmid vector (SEQ ID NO:20).

DETAILED DESCRIPTION OF THE INVENTION

The cloning of the DraIII restriction endonuclease gene from *Deinococcus radiophilus* proved to be challenging. A methylase selection strategy was tried but no methylase expressing clones were isolated. A direct cloning method was then used to clone both the endonuclease and methylase genes. The method described herein by which the DraIII restriction endonuclease is preferably cloned and expressed in the *E. coli* utilizes the following steps:

1. Purify the DraIII restriction endonuclease to near homogeneity and determine its N-terminal as well as a stretch of internal amino acid sequences.

Figure 1:
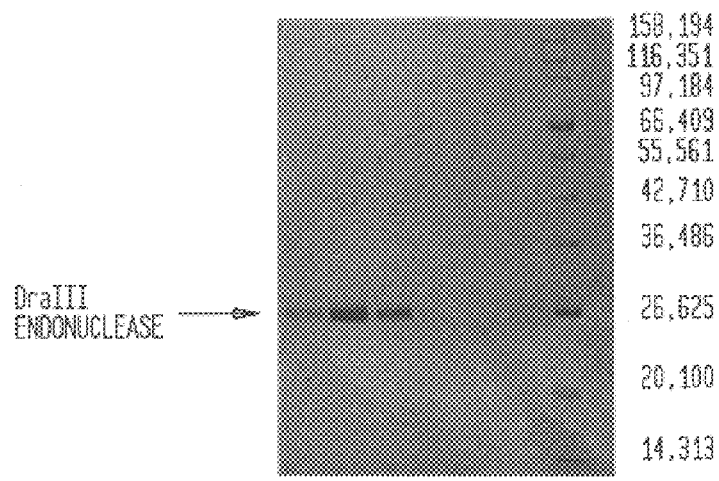
FIG. 1 shows the purified native DraIII endonuclease on a SDS-PAGE.

A unique combination of ion-exchange chromatography columns were use to purify native DraIII restriction endonuclease to near homogeneity. Six column chromatographies were used to purify DraIII endonuclease protein. They included a phosphocellulose column, an Affigel Blue column, another Affigel Blue column, a Heparin Sepharose column, a SourceTM-15Q column, and a Heparin TSK column. The purification yielded a single protein band at approximately 26 kDa on an SDS-PAGE protein following Coomassie blue staining (FIG. 1). The N-terminal 27 amino acid residues were determined by sequential degradation of the purified protein on an automated sequencer. To determine its internal protein sequence, a 5-kDa polypeptide fragment was obtained following cyanogen bromide digestion of the 26-kDa DraIII protein. The sequence of 21 amino acid residues of this 5-kDa was determined. This 21-amino acid sequence differs from the sequence of the N-terminal 27 amino acid residues, suggesting it was derived from internal DraIII protein fragment.

2. Amplification of 5' region of DraIII endonuclease gene and subsequent cloning into plasmid.

Degenerate primers were designed based on the N-terminal and internal amino acid sequences and these primers were used to PCR amplify the 5' end of the endonuclease gene. PCR products were cloned into plasmid pCAB16 and sequenced. The 335-bp PCR fragment which corresponds to the DraIII endonuclease gene was then identified by comparing the amino acid sequences deduced from the cloned DNA with the N-terminal and internal amino acid sequences of the DraIII endonuclease protein.

3. Chromosome walking via inverse PCR to isolate the DraIII endonuclease and methylase genes.

Figure 2:
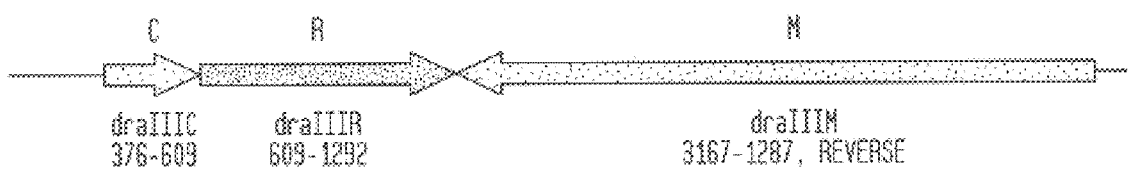
FIG. 2 shows the gene organization of DraIII restriction-modification system. draIIIR: DraIII endonuclease gene; draIIIM: DraIII methylase gene; draIIIC: control gene.

To clone the entire DraIII endonuclease gene as well as its corresponding DNA methylase gene, inverse PCR techniques were adopted to amplify DNA adjacent to the original 335-bp endonuclease gene fragment (Ochman, et al., *Genetics*, 120:621 (1988), Triglia, et al., *Nucl. Acids Res.*, 16:8186 (1988) and Silver and Keerikatte, *J. Cell. Biochem.*, (Suppl.) 13E:306, Abstract No. WH239 (1989)) and the amplified products were sequenced. In total, three rounds of inverse PCR were performed. At that point, three open reading frames (ORF) were identified (FIG. 2). The 684-bp endonuclease gene (draIIIR) encodes a 227-amino acid protein with a deduced molecular weight of 25,170, which agrees with the observed molecular mass of DraIII endonuclease (FIG. 1). A 234-bp small ORF, draIIIC, is located upstream of the draIIIR. It exhibits extensive sequence homology to the control (C) genes found in several other restriction-modification systems (Ives et al., *J. Bacteriology*, 177:6313 (1995)). A 1881-bp ORF, draIIIM, is located downstream, oriented in opposite direction of the draIIIR gene. The protein sequence deduced from draIIIM gene shares significant sequence similarity with other adenine methylases.

4. Expression of DraIII endonuclease gene using pHKUV5 and pHKT7 plasmids.

The two-step method for cloning restriction-modification systems is described in U.S. Pat. No. 5,320,957. The first step includes introducing the methylase gene into a host cell and expressing the gene therein to protect the host cell from corresponding endonuclease digestion by pre-modification of recognition sequences. The second step includes introduction of the endonuclease gene into the pre-modified host cell and subsequent endonuclease production.

DraIII methylase gene, draIIIM, was cloned into a high copy number plasmid, litmus28 (NEBT#306-28), downstream of the lactose promoter ($P_{lac}$). However, the host cell was not fully modified by this construct. A new plasmid, pHKUV5, was engineered to increase the expression level of draIIIM gene. pHKUV5 features a strong, constitutive UV5 promoter ($P_{uv5}$) without the Lac repressor (LacI) binding site, so that the methyltransferase gene will be expressed continuously at high levels. In addition, pHKUV5 also carries a high copy number origin of replication (ColE1), and LacI gene. Because LacI gene is on a high copy number plasmid, it is highly expressed. However, the large amount of LacI won't interfere the expression of the methylase gene from $P_{uv5}$, because the LacI binding site has been deleted from the promoter.

Figure 6:
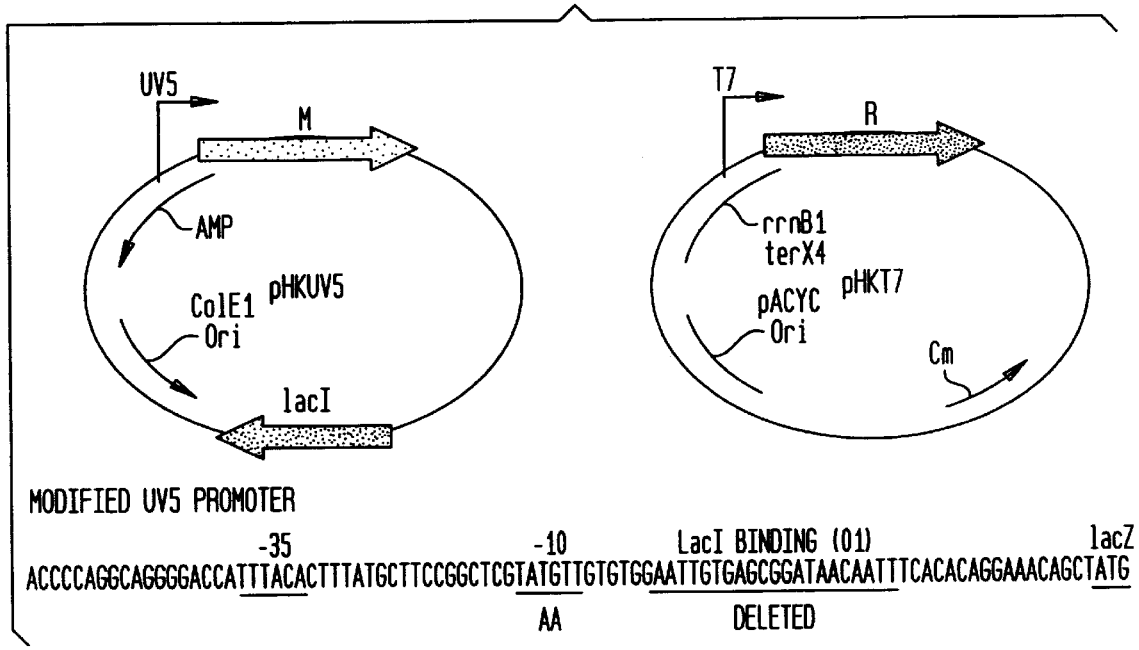
FIG. 6 shows two expression vectors, pHKUV5 and pHKT7 (SEQ ID NO:21).

Plasmid pHKUV5 was engineered from plasmid pUC19 (New England Biolabs, #304). First, synthetic oligonucleotides were used to convert $P_{lac}$ of pUC19 into a stronger UV5 promoter by changing the −10 sequence of $P_{lac}$ from TATGTT to more conserved TATAAT (FIG. 6). In the meantime, the LacI binding site was deleted by the same oligonucleotides. Next, the LacI gene was cloned from a donor plasmid into pHKUV5. The draIIIM gene was then cloned into plasmid pHKUV5 and transformed into *E. coli* cells. The host cell was fully modified by pHKUV5-draIIIM construct.

To express the DraIII endonuclease gene, we constructed a low copy number vector pHKT7. Plasmid pHKT7 contains a controllable T7 promoter which is controlled by LacI. The origin of replication is from plasmid p15A which is compatible with pHKUV5 plasmid. The basal level of expression is extremely low because the T7 promoter is on a low copy number plasmid and the presence of high level of LacI repressor made from high copy number plasmid pHKUV5. The endonuclease gene, draIIIR, was cloned into pHKT7, and then introduced into *E. coli* ER2566 containing pHKUV5-draIIIM. The culture was grow to middle log and was induced by the addition of IPTG to a final concentration of 0.4 mM. The yield of recombinant DraIII endonuclease is $1.6\times10^6$ units per gram cells which is 500-fold higher than the yield of native endonuclease from *Deinococcus radiophilus*.

The following Example is given to additionally illustrate embodiments of the present invention as it is presently preferred to practice. It will be understood that this Example is illustrative, and that the invention is not to be considered as restricted thereto except as indicated in the appended claims.

The references cited above and below are herein incorporated by reference.

EXAMPLE 1

Purification of the DraIII Endonuclease and Determination of Protein Sequence

1. Purification of the DraIII restriction endonuclease from *Deinococcus radiophilus* to near homogeneity:

*Deinococcus radiophilus* cells were propagated at 30° C. The cells were harvested by centrifugation after 20 hours of growth and stored at −70° C. until used. All of the following procedures were performed on ice or at 4° C. 458 g of cell pellet (wet weight) was resuspended in 915 ml of buffer A (20 mM KPO4, 10 mM BME, 0.1 mM EDTA, pH 6.9) supplemented to 0.1 M NaCl and broken with a Manton-Gaulin homogenizer. One ml/L of PMSF (25 mg/ml) was added after the first pass. The extract was centrifuged at 14,000 rpm for 10 minutes at 4° C.

In a beaker, 650 ml P-cell resin (Pharmacia Biotech, Piscataway, N.J.) was mixed/equilibrated with buffer A supplemented with 0.1 M NaCl. The 1200 ml supernatant from the centrifuged crude cell extract was added to the P-cell resin and stirred on ice for 30 minutes. The crude/resin mixture was then centrifuged at 3,000 RPM for 15 minutes. The supernatant (~1200 ml) was poured off as "flow through" and the pellets were resuspended in a total of 800 ml of buffer A supplemented with 0.1 M NaCl. The crude/resin mixture was then poured into a 10 cm×8 cm gravity column and the affluent (~750 ml) was collected as "wash". The column was eluted with a 2 L gradient that ran from 0.1 M NaCl to 1.0 M NaCl in buffer A. Twenty two ml fractions were collected. Fractions were assayed for DraIII restriction activity on lambda DNA. The peak of restriction enzyme activity was found to elute from the column at approximately 1 M NaCl. Fractions 68 to 86 were pooled.

The P-cell pool was diluted to 0.5 M NaCl with buffer A. This 970 ml load was applied to a 214 ml, 5.5 cm×9 cm Affigel Blue column that had been equilibrated buffer A.1 (buffer A supplemented to 0.5 M NaCl). The column was then washed with 275 ml of buffer A.1. A 1 L gravity gradient was run from 0.5 M NaCl to 3.5 M NaCl in Buffer A and then the column was bumped with 300 ml of Buffer B (2 M Guanidine-HCl, 0.1 M NaCl, 20 mM KPO4, 0.1 mM EDTA and 10 mM BME, pH 6.9). DraIII activity was found in the 300 ml bump pool. This pool was dialyzed against 2 L of buffer A.1. The dialyzed pool contained approximately $7.5\times10^6$ units which was loaded onto a 49 ml, 2.5 cm×10 cm Affigel Blue column that had been equilibrated with buffer A.1. The column was washed with 100 ml of buffer A.1 and a 500 ml gravity gradient was run from 0.5 M NaCl to 3.5 M NaCl in buffer A. The column was then bumped with 125 ml of buffer B. The 125 ml bump pool was dialyzed against 2 L of buffer A.1 and then diluted to 0.2 M NaCl with buffer A. DraIII activity assayed on lambda DNA was determined to be approximately $3.75\times10^6$ units in a total of 300 ml.

The fourth column was a 17 ml (1.5 cm×10 cm) Heparin Sepharose column. It was equilibrated with A.2 (buffer A supplemented to 0.2 M NaCl) and the 300 ml sample was loaded to this column. The column was washed with 50 ml of buffer A.2 and a 170 ml gravity gradient was run from 0.2 M to 1.2 M NaCl in buffer A. Four ml fractions were collected and assayed for DraIII activity. Fractions 19–22 (average salt concentration 750 mM) had the most activity and were pooled and dialyzed against 2 L of buffer C (20 mM Tris, 0.1 mM EDTA, 10 mM BME, pH 7.8) supplemented to 100 mM NaCl. The sample was then diluted to 50 mM NaCl with buffer C and the protein concentration was determined to be 1 mg/ml in a 17 ml sample. The sample was then loaded onto a 8 ml HR 10/10 Source-15Q (Pharmacia Biotech, Piscataway, N.J.) column that had been equilibrated with 100 ml of buffer C.1 (buffer C supplemented to 50 mM NaCl). The column was washed with 16 ml of buffer C.1 and a 80 ml gradient was run from 50 mM to 700 mM NaCl in buffer C. Two ml fractions were collected. Activity was found in fractions 9–13 but the majority of the activity was found in fraction 11 (121,000 u/ml). Because the purification goal was a homogeneous protein, the most concentrated fraction (#11) was diluted from approximately 200 mM NaCl to 50 mM NaCl with buffer C.1. The diluted sample was loaded onto a 3.3 ml Heparin 5PW TSK-gel (Toso Haas, Montgomeryville, Pa.) column that was equilibrated with 60 ml of buffer C.1. A 56 ml gradient was run from 50 mM to 1 M NaCl in buffer C and 0.5 ml fractions were collected. DraIII activity was found in fractions 35–40 (approximately 677 mM NaCl). Twenty $\mu$L of the peak fractions (35–40) were loaded onto an SDS-PAGE protein gel and subjected to electrophoresis. The gel was stained with Coomassie blue R-250 and a prominent band at approximately 26.6 kDa corresponding to the DraIII restriction endonuclease activity was observed (FIG. 1). After these six columns, approximately 57,000 units of DraIII activity were purified to near homogeneity.

2. Determining the N-terminal and internal protein sequences of DraIII endonuclease The DraIII restriction endonuclease, prepared as described was subjected to electrophoresis and electroblotted according to the procedure of Matsudaira (Matsudaira, P., *J. Biol. Chem.* 262:10035–10038, 1987), with modifications as previously described (Looney, et al., *Gene* 80:193–208, 1989). The membrane was stained with Coomassie blue R-250 and the protein band of approximately 26.6 kDa was excised and subjected to sequential degradation on an Applied BioSystems Division, Perkin-Elmer Corporation (Foster City, Calif.) Model 407A gas phase protein sequencer (Waite-Rees, et al., *J. Bacteriol.* 173:5207–5219 (1991). The first 27 residues of the 26.6 kDa protein corresponded to M-E-L-C(?)-H-K-T-V-K-S-R-T-A-Y-S-K-X-F-P-X-K-F-Q-L-P-L-G-G(?) (SEQ ID NO:4).

A 5-kDa polypeptide fragment was purified after digesting the 26.6-kDa R.DraIII with Cyanogen Bromide. The N-terminal protein sequence of this 5 kDa was determined as: M-Q-S-L-P-E-I-T-X-L-K-I-X-E-K-A-A-D-Y-X-D-I (SEQ ID NO:5).

EXAMPLE 2

Cloning of the DraIII Restriction-Modification Genes

1. Purification of genomic DNA from *Deinococcus radiophilus*

To prepare the genomic DNA of *Deinococcus radiophilus*, 5 g of cells were resuspended in 10 ml of 25% Sucrose, 50 mM Tris, pH 8.0 and mixed until the solution was homogenous. Five ml of 0.25 M EDTA, pH 8.0 plus 3 ml of freshly-prepared 10 mg/ml lysozyme in 0.25 M Tris-HCl (pH 8.0) was added and the solution was incubated on ice for 2 hours. Twelve ml of Lytic mix (1% Triton-X100, 50 mM Tris, 62 mM EDTA, pH 8.0) and 2.5 ml of 10% SDS were then added and the solution was gently mixed. The solution was extracted with one volume of equilibrated phenol/chloroform (50:50, v/v) and the aqueous phase was recovered. The aqueous solution was then dialyzed against four changes of 2 L of 10 mM Tris-HCl (pH 8.0), 1 mM EDTA. The dialyzed solution was digested with RNase A (100 $\mu$g/ml) at 37° C. for 1 hour. The DNA was precipitated by the addition of 1/10th volume 5 M NaCl and 0.55 volume of 2-propanol and spooled on a glass rod. The DNA was air dried and dissolved in 15 ml TE (10 mM Tris, 1 mM EDTA, pH 8.0) to a concentration of approximately 160 $\mu$g/ml and stored at 4° C.

2. Cloning the 5' region of the DraIII endonuclease gene into pCAB16 pCAB16 was digested with BsaAI by incubating the vector for 1 hour at 37° C. in the conditions described below.

120 $\mu$l pCAB 16 (6–12 $\mu$g)

10 $\mu$l BsaAI (50U)

40 $\mu$l 10X NEB Buffer #3

230 $\mu$l dH$_2$O

The BsaAI in the reaction was heat killed by incubating for 15 minutes at 75° C. The vector was then dephosphorylated by incubating 100 $\mu$l (2 $\mu$g) of digested vector with 1 unit of shrimp alkaline phosphatase in 100 mM MgCl$_2$ for 1 hour at 37° C.

Degenerate primers were designed based on the following N-terminal and internal amino acid sequences: 1) M-E-L-C-H-K (SEQ ID NO:6) (N-terminal) and 2) E-K-A-A-D-Y (SEQ ID NO:7) (internal). They were designed to hybridize with the 5' end of the DraIII endonuclease gene and with an internal segment of the gene respectively. The primers are oriented in opposite directions relative to each other.

Primer N-terminal 5' ATGGARYTNTGYCAYAAR 3' (SEQ ID NO:8)

Primer internal 5' TARTCNGCNGCYTTYTC 3' (SEQ ID NO:9)

These primers were synthesized and each was kinased by incubating 1 $\mu$g of primer with 10 units of T4 Polynucleotide Kinase, 2 $\mu$l 10X T4 Polynucleotide Kinase, and 1 $\mu$l of 10 mM ATP, in a 20 $\mu$l reaction volume at 37° C. for 30 minutes. The kinase was heat inactivated by incubating the reaction at 65° C. for 10 min.

In the reaction that was successful in amplifying the product, a reaction mix was made by combining:

40 $\mu$l of 10X Vent® Thermo Pol Buffer

40 $\mu$l of 2 mM dNTP solution

60 $\mu$l of kinased primer N-term (10 $\mu$M final)

60 $\mu$l of kinased primer internal (10 $\mu$M final)

8 $\mu$l of 100 mM MgSO$_4$

4 $\mu$l of purified bacterial DNA template (~400 ng)

180 $\mu$l dH$_2$O

8 $\mu$l (4 units) of Vent® Exo-polymerase NEB#257

The PCR amplification conditions were: 35 cycles of 95° C. for 30 seconds, 50° C. for 60 seconds and 72° C. for 45 seconds. 100 $\mu$l of the PCR reaction was electrophoresed on a 3% low melting temperature agarose gel (NuSieve Agarose, FMC BioProducts, Rockland, Me.) in TAE buffer (40 mM Tris-Acetate, pH 8, 1 mM EDTA). The approximately 335-bp DNA band was excised out and the gel slice was incubated at 65° C. for 10 minutes. The temperature was reduced to 40° C. and an in-gel ligation was performed by combining the following at 40° C.:

2.7 μl prepared pCAB16 (50 ng)
5 μl PCR product (20 ng)
5 μl 10X T4 DNA Ligase Buffer
1 μl T4 DNA Ligase (400 units)
1 μl Beta-Agarase (1 unit)
35.3 μl dH₂O The reaction was incubated at 37° C. for one hour and then at 16° C. overnight. Ten μl of the overnight ligation reaction was transformed into 50 μl of *E. coli* ER2502 competent cells by combining the DNA and cells and incubating on ice for 20 minutes followed by 2 minutes at 37° C. The entire volume was plated on an Ampicillin LB plate and incubated overnight at 37° C. Colonies that grew were inspected for the correct plasmid construct by purifying the plasmid DNA using Qiagen QIAprep Spin Miniprep Kit and digesting with BsiHKAI to see if the PCR product was cloned into the vector.

10 μl miniprep
2 μl 1 mg/ml BSA
2 μl 10X NEB #3
1 μl BsiHKAI
5 μl dH₂O

The above reaction was incubated at 65° C. for 1 hour. Minipreps containing the correct size insert were sequenced. The DNA sequence was translated in six reading frames to check whether the deduced amino acid sequence corresponds with the N-terminal and internal amino acid sequence of DraIII protein.

3. Chromosome walking via inverse PCR to isolate the DraIII endonuclease and methylase genes A) Prepare genomic DNA—Three templates were prepared for three consecutive inverse PCR reactions; Sau3AI, SspI and NlaIII. In the case of Sau3AI, 1.5 μg of bacterial DNA was digested with 20 units of Sau3AI restriction endonuclease in 1X Sau3AI buffer supplemented with BSA to a final concentration of 0.1 mg/ml in a 50 μl reaction volume. In the case of SspI, 1.5 μg of bacterial DNA was digested with 25 units of SspI restriction endonuclease in 1X SspI buffer in a 50 μl reaction volume. The NlaIII template was prepared by digesting 1.5 μg of bacterial DNA with 50 units of NlaIII restriction endonuclease in 1X NEBbuffer 4 supplemented with BSA to a final concentration of 0.1 mg/ml in a 50 μl reaction volume. All three reactions were incubated at 37° C. for one hour, phenol/chloroform extracted, ethanol precipitated, resuspended in 40 μl of dH₂O and the final concentrations were deduced by running 13 μl on a 1% agarose gel. The digests were then circularized by incubating the remaining 37 μl (~1 μg) in 1X T4 DNA Ligase Buffer with 3000 units of T4 DNA Ligase in a 500 μl reaction volume at 16° C. overnight. A portion of this circularization ligation reaction was then used as the template for subsequent inverse PCR reactions.

B) Sau3AI inverse PCR—A set of inverse PCR primers was synthesized based on the DNA sequence of the piece of the DraIII endonuclease gene cloned into pCAB16:

5' CAGCTTGGAAGAGTTCACAG 3' (179-181) (SEQ ID NO:10)

5' CCCCTGTAGTCATAGTTGCA 3' (179-182) (SEQ ID NO:11)

Inverse PCR was carried out using primers 179-181 and 179-182 and the above mentioned Sau3AI DNA template. A 1.7 Kb product was observed from the Sau3AI circular template PCR reaction. This product was gel purified and resuspended in 40 μl dH₂O. The PCR product was then sequenced using an ABI 373 automated sequencing system according to the manufacturer's instructions, using the PCR primers above as the sequencing primers. The Sau3AI inverse PCR product contained new DNA sequence both upstream and downstream of the original 5' piece of the draIIIR gene. The entire coding region of a control protein and part of an ORF that according to BLAST analysis could be a glycine dehydrogenase were found upstream while downstream the entire endonuclease ORF was identified as well as part of an adenine methylase ORF (FIG. 2).

C) SspI inverse PCR reaction—Two inverse PCR primers complementary to newly read sequence from the Sau3AI PCR product were then synthesized, as below, and used in an inverse PCR reaction. Template preparation, inverse PCR, purification and DNA sequencing were performed as above but SspI was used to create the template as opposed to Sau3AI. A 1.3 Kb PCR product was generated and sequenced. The sequence continued to reveal more of the draIIIM gene (1181 bp).

5' ATTCTCTTCGGTGACC 3' (181-42) (SEQ ID NO:12)

5' TCGAGGTGCATAGTACAA 3' (181-43) (SEQ ID NO:13)

D) NlaIII inverse PCR reaction—Two inverse PCR primers complementary to newly read sequence from the SspI PCR product were then synthesized, as below, and used in an inverse PCR reaction. Template preparation, inverse PCR, purification and DNA sequencing were performed as above but NlaIII was used to create the template. A 600-bp PCR product was generated and sequenced. The 250-bp of novel sequence revealed the rest of the draIIIM gene.

5' TAGGGCCAACTATTCGCGGA 3' (182-119) (SEQ ID NO:14)

5' TCAAAGCCTGAAAGGCATCTC 3' (182-120) (SEQ ID NO:15)

EXAMPLE 3

Expression of the DraIII Restriction Endonuclease

1. Cloning the DraIII methylase on a compatible vector

The DraIII methylase gene (draIIIR) was expressed by inserting the gene into an expression vector, pHKUV5, directly downstream of the strong UV5 promoter. To accomplish this, two oligonucleotide primers were made utilizing the DNA sequence data. The forward oligonucleotide primer contained a PstI site to facilitate cloning, a stop codon in frame with the lacZ gene to terminate translation of the lacZ protein, a ribosome binding site (RBS, underlined) and 20 nucleotides complementary to *Deinococcus radiophilus* DNA for hybridization:

5'-AAAACTGCAGATA<u>AGGAGG</u>TGATCGTATGAC GAATGTGGAACAAGT-3' (194-89) (SEQ ID NO:16)

The reverse primer was designed to hybridize to *Deinococcus radiophilus* DNA at the 3' end of the DraIII gene. It contained a BamHI restriction site to facilitate cloning and a DraIII site which was used to test the in vivo DraIII methylase activity.

5'-CGCGGATCCCACTGTGTGCTATAGCTCTGCTTC ATGTGC-3' (194-144) (SEQ ID NO:17)

These two primers were used to amplify the draIIIM gene from *Deinococcus radiophilus* genomic DNA by combining:

10 μl 10X Vent® ThermoPol Buffer
10 μl of 2 mM dNTPs
0.5 μl (150 ng) *Deinococcus radiophilus* genomic DNA 1 μl primer 194-89 (75 ng)
1 μl primer 194-144 (75 ng)
75.5 μl dH$_2$O
1 μl (0.1 units) Deep Vent® polymerase
1 μl Taq DNA polymerase (5 units)

and amplifying for 25 cycles at 95° C. for 30 seconds, 50° C. for 1 minute and 72° C. for 2 minutes. The amplification product was purified using the Promega Wizard PCR Prep Kit. (Madison, Wis.) One μg of pHKUV5 vector and the remaining PCR product (~2 μg) were both digested with 20 units of BamHI and 20 units of PstI, supplemented with 0.1 mg/ml BSA in 1X NEB BamHI buffer in a 50 μl reaction that was incubated at 37° C. for one hour. The digests were run on a 1% low melting temperature NuSieve agarose gel in TAE buffer. The PCR and vector DNA bands were excised out and the gel slices were incubated at 65° C. for 10 minutes. The temperature was reduced to 40° C. and an in-gel ligation was performed by combining the following at 40° C.:

7.0 μl prepared pHKUV5 (100 ng)
7 μl methylase PCR product (200 ng)
5 μl 10X T4 DNA Ligase Buffer
1 μl T4 DNA Ligase (400 units)
1 μl Beta-Agarase (1 unit)
29 μl dH$_2$O The reaction was incubated at 37° C. for one hour and ten μl of the ligation reaction was transformed into *E. coli* strain ER2566. Individual colonies were isolated and analyzed by digesting minipreps with the cloning enzymes to ensure that the methylase gene had indeed been cloned into the vector:

5 μl miniprep
2 μl 10X BamHI buffer
2 μl 1 mg/ml BSA
1 μl PstI (20 U)
1 μl BamHI (20 U)
9 μl dH$_2$O The digests were incubated at 37° C. for one hour.

The minipreps that were the correct construct were then digested with PstI to linearize the plasmid and then with DraIII to check for methylase protection:

5 μl miniprep
2 μl 10X NEBuffer 3
2 μl 1 mg/ml BSA
1 μl PstI (20 U)
1 μl DraIII (1 U)
9 μl dH$_2$O The digests were incubated at 37° C. for one hour and 1 μl of a clone that was resistant to DraIII digestion was transformed into ER2566 cells for the purpose of making calcium chloride competent cells.

2. Cloning and expression of the DraIII endonuclease gene

The DraIII endonuclease gene (draIIIR) was expressed by inserting the gene into a expression vector, pHKT7, directly downstream of a strong inducible T7 promoter and a conserved ribosome binding site (RBS). To accomplish this, two oligonucleotide primers were made utilizing the DNA sequence data. The forward oligonucleotide primer contained a NdeI site to facilitate cloning, an ATG start codon of the DraIII endonuclease gene and 21 nucleotides complementary to *Deinococcus radiophilus* DNA for hybridization:

5'-GGAATTCCATATGGAGTTGTGCCACAAGACT-3'
(194-93) (SEQ ID NO:18)

The reverse primer was designed to hybridize to *Deinococcus radiophilus* DNA at the 3 end of the draIIIR gene. It contained a XhoI restriction site to facilitate cloning.

5'-AAAATCTCGAGCTATAGCATTTTTACGCG-3'
(184-58) (SEQ ID NO:19)

These two primers were used to amplify the draIIIR gene from *Deinococcus radiophilus* genomic DNA by combining:

30 μl 10X Vent® ThermoPol Buffer
30 μl of 2 mM dNTPs
1.5 μl (300 ng) *Deinococcus radiophilus* genomic DNA
3 μl primer 194-93 (225 ng)
3 μl primer 184-58 (225 ng)
226.5 μl dH$_2$O
3 μl (0.3 units) Deep Vent® polymerase
3 μl Taq DNA polymerase (15 units)

and amplifying for 25 cycles at 95° C. for 30 seconds, 50° C. for 1 minute and 72° C. for 1.5 minutes. The amplification product was purified using the Promega Wizard PCR Prep Kit (Madison, Wis.). 1 μg of pHKT7 vector and the remaining PCR product (~400 ng) were both digested with 20 units of BamHI and 20 units of XhoI, supplemented with 0.1 mg/ml BSA in 1X NEB BamHI buffer in a 50 μl reaction that was incubated at 37° C. for one hour. The digests were run on a 1% low melting-point NuSieve agarose gel in TAE buffer. The PCR and vector DNA bands (678 and 3500 bp respectively) were cut out and the gel slices were incubated at 65° C. for 10 minutes. The temperature was reduced to 40° C. and an in-gel ligation was performed by combining the following at 40° C.:

9.0 μl prepared pHKT7 (100 ng)
50 μl endonuclease PCR product (50 ng)
6.8 μl 10X T4 DNA Ligase Buffer
1 μl T4 DNA Ligase (400 units)
1 μl Beta-Agarase (1 unit)

The reaction was incubated at 37° C. for one hour. Seven μl of the ligation reaction was transformed into *E. coli* strain ER2566 previously modified with the DraIII methylase gene. Transformants were analyzed and one contained the draIIIR gene. This plasmid construct, pHKT7-draIIIR, was selected for producing the DraIII endonuclease. The *E. coli* strain which contains both pHKT7-draIIIR and pHKUV5-draIIIM plasmids was designated as NEB #1176. The yield of recombinant DraIII in strain NEB #1176 was approximately 1.6×10^6 units/gram of cells.

3. Producing the recombinant DraIII restriction endonuclease from *E. coli* NEB #1176

*E. coli* NEB #1176 was grown to mid-log phase in a fermenter containing L-broth medium with ampicillin (100 μg/ml) and chloramphenicol (50 μg/ml). The culture was induced by the addition of IPTG to a final concentration of 0.4 mM and allowed to continue growing for 16 hours. The cells were harvested by centrifugation and may be stored at −70° C. or used immediately.

Purification of the DraIII restriction endonuclease from NEB #1176 can be accomplished by a combination of standard protein purification techniques, such as affinity-chromatography or ion-exchange chromatography, as outlined in Example 1 above. The DraIII restriction endonuclease obtained from this purification is substantially pure and free of non-specific endonuclease and exonuclease contamination.

A sample of the *E. coli* NEB#1176 which contains both pHKUV5-draIIIM and pHKT7-draIIIR plasmids has been deposited under the terms and conditions of the Budapest Treaty with the American Type Culture Collection on Jan 22, 1999 and received ATCC Accession Number 207087.

What is claimed is:

1. Isolated DNA coding for the DraIII restriction endonuclease, wherein the isolated DNA is obtainable from *Deinococcus radiophilus*.

2. A recombinant DNA plasmid comprising the pHKUV5 vector into which a DNA segment coding for the DraIII methylase has been inserted.

3. A vector which comprises the isolated DNA of claim 1.

4. A host cell transformed by the cloning vectors of claims 2 or 3.

5. A method of producing a DraIII restriction endonuclease comprising culturing a host cell transformed with the vector of claim 2 or 3 under conditions suitable for expression of said endonuclease.

6. A novel method of cloning and expressing DraIII endonuclease gene comprising a unique two plasmid system of pHKUV5 and pHKT7.

* * * * *

UNITED STATES PATENT AND TRADEMARK OFFICE
CERTIFICATE OF CORRECTION

PATENT NO. : 6,048,719
DATED : April 11, 2000
INVENTOR(S) : Huimin Kong, et. al.

It is certified that error appears in the above-indentified patent and that said Letters Patent is hereby corrected as shown below:

| | |
|---|---|
| Column 4, line 10 | replace "FIG. 4 shows" with --FIGS. 4A, 4B and 4C show-- |
| Column 4, line 16 | replace "FIG. 7 shows" with --FIGS. 7A, 7B and 7C show-- |
| Column 4, line 29 | delete "the" first occurrence |
| Column 4, line 34 | replace "use" with --used-- |
| Column 5, line 43 | after "interfere" insert --with-- |
| Column 6, line 1 | replace "grow" with --grown-- |
| Column 7, line 14 | replace "a" with --an-- |
| Column 7, line 18 | replace "a" with --an-- |
| Column 7, line 41 | after "described" insert --,-- |
| Column 9, lines 30-31 | replace "corresponds" with --corresponded-- |
| Column 11, line 55 | replace "a" with --an-- |
| Column 11, line 60 | replace "a" with --an-- |
| Column 5, line 32 | replace "(NEBT#306-28)" with --(NEB#306-28)-- |
| Claim 3, line 1 | after "A" insert "cloning" |
| Claim 4, line 1 | delete "cloning" |

Signed and Sealed this

Twentieth Day of March, 2001

Attest:

NICHOLAS P. GODICI

Attesting Officer    Acting Director of the United States Patent and Trademark Office

SEQUENCE LISTING

<160> NUMBER OF SEQ ID NOS: 21

<210> SEQ ID NO 1
<211> LENGTH: 684
<212> TYPE: DNA
<213> ORGANISM: Deinococcus radiophilus
<220> FEATURE:
<221> NAME/KEY: CDS
<222> LOCATION: (1)..(681)

<400> SEQUENCE: 1

| atg | gaa | ttg | tgc | cat | aaa | act | gtc | aag | tca | aga | acc | gcc | tac | tcc | aaa | 48 |
|---|---|---|---|---|---|---|---|---|---|---|---|---|---|---|---|---|
| Met | Glu | Leu | Cys | His | Lys | Thr | Val | Lys | Ser | Arg | Thr | Ala | Tyr | Ser | Lys | |
| 1 | | | | 5 | | | | | 10 | | | | | 15 | | |

| cat | ttt | cct | cac | aaa | tgt | cag | ctt | cct | tta | ggt | cat | agt | ggc | aaa | tgt | 96 |
|---|---|---|---|---|---|---|---|---|---|---|---|---|---|---|---|---|
| His | Phe | Pro | His | Lys | Cys | Gln | Leu | Pro | Leu | Gly | His | Ser | Gly | Lys | Cys | |
| | | | | 20 | | | | | 25 | | | | | 30 | | |

| ctc | gaa | ttt | cct | ttt | tta | gtc | agc | ctt | tca | aaa | acg | cat | cct | cga | atc | 144 |
|---|---|---|---|---|---|---|---|---|---|---|---|---|---|---|---|---|
| Leu | Glu | Phe | Pro | Phe | Leu | Val | Ser | Leu | Ser | Lys | Thr | His | Pro | Arg | Ile | |
| | | 35 | | | | | 40 | | | | | 45 | | | | |

| gca | gct | aag | att | gtt | cga | gat | gca | act | atg | act | aca | ggg | gca | gct | tgg | 192 |
|---|---|---|---|---|---|---|---|---|---|---|---|---|---|---|---|---|
| Ala | Ala | Lys | Ile | Val | Arg | Asp | Ala | Thr | Met | Thr | Thr | Gly | Ala | Ala | Trp | |
| 50 | | | | | 55 | | | | | 60 | | | | | | |

| aag | agt | tca | cag | gct | ggg | cct | aat | aga | atg | cca | agg | tat | gtt | gca | ata | 240 |
|---|---|---|---|---|---|---|---|---|---|---|---|---|---|---|---|---|
| Lys | Ser | Ser | Gln | Ala | Gly | Pro | Asn | Arg | Met | Pro | Arg | Tyr | Val | Ala | Ile | |
| 65 | | | | | 70 | | | | | 75 | | | | | 80 | |

| ctt | gac | gat | gat | att | cta | ctg | gag | aaa | ttc | aac | ctt | gat | atg | cag | tcc | 288 |
|---|---|---|---|---|---|---|---|---|---|---|---|---|---|---|---|---|
| Leu | Asp | Asp | Asp | Ile | Leu | Leu | Glu | Lys | Phe | Asn | Leu | Asp | Met | Gln | Ser | |
| | | | | 85 | | | | | 90 | | | | | 95 | | |

| cta | ccc | gag | att | act | aga | ttg | aaa | att | agg | gaa | aag | gcc | gca | gat | tat | 336 |
|---|---|---|---|---|---|---|---|---|---|---|---|---|---|---|---|---|
| Leu | Pro | Glu | Ile | Thr | Arg | Leu | Lys | Ile | Arg | Glu | Lys | Ala | Ala | Asp | Tyr | |
| | | | 100 | | | | | 105 | | | | | 110 | | | |

| gat | tca | tgt | ata | gat | gta | gcc | aga | aag | tta | act | tgg | cta | gcc | tat | caa | 384 |
|---|---|---|---|---|---|---|---|---|---|---|---|---|---|---|---|---|
| Asp | Ser | Cys | Ile | Asp | Val | Ala | Arg | Lys | Leu | Thr | Trp | Leu | Ala | Tyr | Gln | |
| | | 115 | | | | | 120 | | | | | 125 | | | | |

| ttg | cac | ggt | gcg | cca | ata | ccc | gat | agt | ttc | aca | aag | aat | tat | tta | gaa | 432 |
|---|---|---|---|---|---|---|---|---|---|---|---|---|---|---|---|---|
| Leu | His | Gly | Ala | Pro | Ile | Pro | Asp | Ser | Phe | Thr | Lys | Asn | Tyr | Leu | Glu | |
| | 130 | | | | | 135 | | | | | 140 | | | | | |

| gaa | ttc | ttt | ggg | cca | atg | gtg | gcg | ggg | tct | aca | aat | tgt | gag | att | tgc | 480 |
|---|---|---|---|---|---|---|---|---|---|---|---|---|---|---|---|---|
| Glu | Phe | Phe | Gly | Pro | Met | Val | Ala | Gly | Ser | Thr | Asn | Cys | Glu | Ile | Cys | |
| 145 | | | | | 150 | | | | | 155 | | | | | 160 | |

| aag | ctc | cct | cta | acc | att | gac | cta | ttt | tcc | gaa | aat | agg | gta | ggt | aag | 528 |
|---|---|---|---|---|---|---|---|---|---|---|---|---|---|---|---|---|
| Lys | Leu | Pro | Leu | Thr | Ile | Asp | Leu | Phe | Ser | Glu | Asn | Arg | Val | Gly | Lys | |
| | | | | 165 | | | | | 170 | | | | | 175 | | |

| gct | gcc | gtg | gaa | act | gcc | cac | aag | aca | ccc | aga | tta | cat | aat | gcc | gag | 576 |
|---|---|---|---|---|---|---|---|---|---|---|---|---|---|---|---|---|
| Ala | Ala | Val | Glu | Thr | Ala | His | Lys | Thr | Pro | Arg | Leu | His | Asn | Ala | Glu | |
| | | | 180 | | | | | 185 | | | | | 190 | | | |

| aat | gta | gga | ttt | gcc | cat | agg | ttt | tgc | aat | gtg | gca | cag | ggg | aat | aaa | 624 |
|---|---|---|---|---|---|---|---|---|---|---|---|---|---|---|---|---|
| Asn | Val | Gly | Phe | Ala | His | Arg | Phe | Cys | Asn | Val | Ala | Gln | Gly | Asn | Lys | |
| | | 195 | | | | | 200 | | | | | 205 | | | | |

| tca | cta | gac | gaa | ttt | tat | ctg | tgg | atg | gaa | gag | gtt | ttg | act | cgc | gta | 672 |
|---|---|---|---|---|---|---|---|---|---|---|---|---|---|---|---|---|
| Ser | Leu | Asp | Glu | Phe | Tyr | Leu | Trp | Met | Glu | Glu | Val | Leu | Thr | Arg | Val | |
| | 210 | | | | | 215 | | | | | 220 | | | | | |

| aaa | atg | cta | tag | | | | | | | | | | | | | 684 |
|---|---|---|---|---|---|---|---|---|---|---|---|---|---|---|---|---|
| Lys | Met | Leu | | | | | | | | | | | | | | |
| 225 | | | | | | | | | | | | | | | | |

<210> SEQ ID NO 2
<211> LENGTH: 1881
<212> TYPE: DNA

<213> ORGANISM: Deinococcus radiophilus
<220> FEATURE:
<221> NAME/KEY: CDS
<222> LOCATION: (1)..(1878)
<223> OTHER INFORMATION: At position 1195 and 1564: "N" = A, C, G, or T

<400> SEQUENCE: 2

```
atg acg aat gtg gaa caa gtt gtt gcc gat tac cca agg aga ttt aag      48
Met Thr Asn Val Glu Gln Val Val Ala Asp Tyr Pro Arg Arg Phe Lys
 1               5                  10                  15 aac ctt tac tac aga ctt tac aca aat agt aat tct agt cgc gcc gag      96
Asn Leu Tyr Tyr Arg Leu Tyr Thr Asn Ser Asn Ser Ser Arg Ala Glu
             20                  25                  30 aaa cta att tac gaa ttg tcg cga ata ctt ttg ctt aaa ttg gcg gcg     144
Lys Leu Ile Tyr Glu Leu Ser Arg Ile Leu Leu Leu Lys Leu Ala Ala
         35                  40                  45 gag agg cga aat gga aaa acg gtt tta agt aac ttt atc gat gat cca     192
Glu Arg Arg Asn Gly Lys Thr Val Leu Ser Asn Phe Ile Asp Asp Pro
 50                  55                  60 gtc aat aat caa gaa gac ctg ctt aag ttg ggt gga gat gaa ttt gaa     240
Val Asn Asn Gln Glu Asp Leu Leu Lys Leu Gly Gly Asp Glu Phe Glu
 65                  70                  75                  80 ata ttg gaa aat caa gat aaa tat ttt tcg ctt gat ctg tct tcg gtt     288
Ile Leu Glu Asn Gln Asp Lys Tyr Phe Ser Leu Asp Leu Ser Ser Val
                 85                  90                  95 gtt tcg gca ttt gcg gag ata tcc gat att gaa ctt cat agt gcc cct     336
Val Ser Ala Phe Ala Glu Ile Ser Asp Ile Glu Leu His Ser Ala Pro
            100                 105                 110 gga cat att gtt gga gat gcc ttt cag gct ttg ata ggg cca act att     384
Gly His Ile Val Gly Asp Ala Phe Gln Ala Leu Ile Gly Pro Thr Ile
        115                 120                 125 cgc gga gat aaa ggg cag ttt ttc aca cct aag aat tta acg gat gcg     432
Arg Gly Asp Lys Gly Gln Phe Phe Thr Pro Lys Asn Leu Thr Asp Ala
    130                 135                 140 ata ata aag att tta tcc cct aag cct gga gac aaa att att gat cct     480
Ile Ile Lys Ile Leu Ser Pro Lys Pro Gly Asp Lys Ile Ile Asp Pro
145                 150                 155                 160 gcc tgt gga acg gga gga ttt ctt tct tca tgt caa gca tat tgg gaa     528
Ala Cys Gly Thr Gly Gly Phe Leu Ser Ser Cys Gln Ala Tyr Trp Glu
                165                 170                 175 ttg aca tat aaa gat cct act gct cgc tat gaa atc tta ggt att gat     576
Leu Thr Tyr Lys Asp Pro Thr Ala Arg Tyr Glu Ile Leu Gly Ile Asp
            180                 185                 190 aaa gac gcc gat atg gcc atg cta tct agt gcg ttg cta gaa att tca     624
Lys Asp Ala Asp Met Ala Met Leu Ser Ser Ala Leu Leu Glu Ile Ser
        195                 200                 205 acc aac gga ttt gct aag gtg gta aac tca gac tca tta aaa ttt att     672
Thr Asn Gly Phe Ala Lys Val Val Asn Ser Asp Ser Leu Lys Phe Ile
    210                 215                 220 att gac aat cct caa tac gaa gaa cag ttt gat ata gtt gtg gca aat     720
Ile Asp Asn Pro Gln Tyr Glu Glu Gln Phe Asp Ile Val Val Ala Asn
225                 230                 235                 240 ccg ccg ttt ggt acg aaa att aaa gta gat aat aag gct ata cta aaa     768
Pro Pro Phe Gly Thr Lys Ile Lys Val Asp Asn Lys Ala Ile Leu Lys
                245                 250                 255 gat tac caa ctc ggt cac tca tgg aaa gtg gaa aat ggt act cta tgt     816
Asp Tyr Gln Leu Gly His Ser Trp Lys Val Glu Asn Gly Thr Leu Cys
            260                 265                 270 cca agc aga cac att ctt ggt gcg caa gac cca caa att ctt ttt ata     864
Pro Ser Arg His Ile Leu Gly Ala Gln Asp Pro Gln Ile Leu Phe Ile
        275                 280                 285
```

```
gag ttg tgc gtg aag ctt ctc aag gaa aat ggt agg atg gct ctt ata      912
Glu Leu Cys Val Lys Leu Leu Lys Glu Asn Gly Arg Met Ala Leu Ile
    290                 295                 300 tta ccg gag gga gtg ttc ggt ggg aag tca tca gaa tat gtg tgg gaa      960
Leu Pro Glu Gly Val Phe Gly Gly Lys Ser Ser Glu Tyr Val Trp Glu
305                 310                 315                 320 tat ctg aaa aat aga ggt ata gtt ttt gcc tta att gat tgt ccg cga     1008
Tyr Leu Lys Asn Arg Gly Ile Val Phe Ala Leu Ile Asp Cys Pro Arg
                325                 330                 335 aca act ttc cag cca tac acg gat att aaa act aat gtg ctt ttc ttc     1056
Thr Thr Phe Gln Pro Tyr Thr Asp Ile Lys Thr Asn Val Leu Phe Phe
            340                 345                 350 aaa aaa acg aaa gaa atg ccg gaa gaa aaa acg cag gta gct gta gct     1104
Lys Lys Thr Lys Glu Met Pro Glu Glu Lys Thr Gln Val Ala Val Ala
        355                 360                 365 aaa agg tgc ggt cat gat aag cgc ggc cgc act cac tac cct tca gga     1152
Lys Arg Cys Gly His Asp Lys Arg Gly Arg Thr His Tyr Pro Ser Gly
    370                 375                 380 ctc tcc gtt cca gat gat ttt gcg gat ata gca aat cta ttt nat gag     1200
Leu Ser Val Pro Asp Asp Phe Ala Asp Ile Ala Asn Leu Phe Xaa Glu
385                 390                 395                 400 ggt ata gaa aac agg atc tgg aaa tct gtc tgt ttg aaa aag gaa tat     1248
Gly Ile Glu Asn Arg Ile Trp Lys Ser Val Cys Leu Lys Lys Glu Tyr
                405                 410                 415 aga gtc cca aga tat tat ttc aat gat gat gaa gca ggc aaa ttg gac     1296
Arg Val Pro Arg Tyr Tyr Phe Asn Asp Asp Glu Ala Gly Lys Leu Asp
            420                 425                 430 aac ata ggt caa gtt ata acc att ggt gag tta att aga atg gga gtt     1344
Asn Ile Gly Gln Val Ile Thr Ile Gly Glu Leu Ile Arg Met Gly Val
        435                 440                 445 ttg aaa ata aga aaa ggt cac gaa gtt ggc tca gaa aac tat ggt acg     1392
Leu Lys Ile Arg Lys Gly His Glu Val Gly Ser Glu Asn Tyr Gly Thr
    450                 455                 460 ggt gat att ccg ttc ata aga acc tcc gac ata aat aat ttg gag ttt     1440
Gly Asp Ile Pro Phe Ile Arg Thr Ser Asp Ile Asn Asn Leu Glu Phe
465                 470                 475                 480 tct tcc gat ccc aca aat tct gtc agc gaa gaa ata tat gaa atg tat     1488
Ser Ser Asp Pro Thr Asn Ser Val Ser Glu Glu Ile Tyr Glu Met Tyr
                485                 490                 495 tcg aaa aaa cag aat atc gcc gcc ggg gac ata tta atg gca gta gat     1536
Ser Lys Lys Gln Asn Ile Ala Ala Gly Asp Ile Leu Met Ala Val Asp
            500                 505                 510 ggg aga tac aga att gga aaa acc gct ntg gtc acc gaa gag aat tcg     1584
Gly Arg Tyr Arg Ile Gly Lys Thr Ala Xaa Val Thr Glu Glu Asn Ser
        515                 520                 525 agg tgc ata gta caa agt cat ata aaa ata tta tca gta gaa ttt aac     1632
Arg Cys Ile Val Gln Ser His Ile Lys Ile Leu Ser Val Glu Phe Asn
    530                 535                 540 agt tta ata aat aac tat gaa tta tta tat atg tta aat ttg gcc gaa     1680
Ser Leu Ile Asn Asn Tyr Glu Leu Leu Tyr Met Leu Asn Leu Ala Glu
545                 550                 555                 560 gtg cag aat caa gtt cgg aat atg gtt ttt gtt caa tca aca ctt ggt     1728
Val Gln Asn Gln Val Arg Asn Met Val Phe Val Gln Ser Thr Leu Gly
                565                 570                 575 act cta ggc aat agg tta gag cag gta aag att gca ata cct cga cgc     1776
Thr Leu Gly Asn Arg Leu Glu Gln Val Lys Ile Ala Ile Pro Arg Arg
            580                 585                 590 aat agc gaa tgg gat aaa atg ata gcc gga ttt aag cat att ttg gaa     1824
Asn Ser Glu Trp Asp Lys Met Ile Ala Gly Phe Lys His Ile Leu Glu
```

-continued

```
                595                 600                 605
gag agg agt aga ctg ctg gta tct ata cgc gga ctg gca cat gaa gca      1872
Glu Arg Ser Arg Leu Leu Val Ser Ile Arg Gly Leu Ala His Glu Ala
    610                 615                 620 gag cta tag                                                          1881
Glu Leu
625

<210> SEQ ID NO 3
<211> LENGTH: 234
<212> TYPE: DNA
<213> ORGANISM: Deinococcus radiophilus
<220> FEATURE:
<221> NAME/KEY: CDS
<222> LOCATION: (1)..(231)

<400> SEQUENCE: 3 atg agt gat tcg ggc gct att gct ata ggt ttc gca att aag cgg ctt       48
Met Ser Asp Ser Gly Ala Ile Ala Ile Gly Phe Ala Ile Lys Arg Leu
  1               5                  10                  15 aga agc tcc aag aag cta tct caa gag agc ttg gca gaa atg tct ggt       96
Arg Ser Ser Lys Lys Leu Ser Gln Glu Ser Leu Ala Glu Met Ser Gly
                 20                  25                  30 att cac cgc act tat atc agt tca ata gag cgc gga gag cga aac gtc      144
Ile His Arg Thr Tyr Ile Ser Ser Ile Glu Arg Gly Glu Arg Asn Val
             35                  40                  45 ggg ata aac atg ctt cta tct att ctt gac gca ttg gaa cag aaa ccc      192
Gly Ile Asn Met Leu Leu Ser Ile Leu Asp Ala Leu Glu Gln Lys Pro
         50                  55                  60 tcc agc ttc ttt agg gag ctg gaa gac gag ggg gta ttt taa              234
Ser Ser Phe Phe Arg Glu Leu Glu Asp Glu Gly Val Phe
     65                  70                  75

<210> SEQ ID NO 4
<211> LENGTH: 28
<212> TYPE: PRT
<213> ORGANISM: Deinococcus radiophilus
<220> FEATURE:
<223> OTHER INFORMATION: At position 17 and 20: "Xaa" = any amino acid

<400> SEQUENCE: 4

Met Glu Leu Cys His Lys Thr Val Lys Ser Arg Thr Ala Tyr Ser Lys
  1               5                  10                  15

Xaa Phe Pro Xaa Lys Phe Gln Leu Pro Leu Gly Gly
                 20                  25

<210> SEQ ID NO 5
<211> LENGTH: 22
<212> TYPE: PRT
<213> ORGANISM: Deinococcus radiophilus
<220> FEATURE:
<223> OTHER INFORMATION: At positions 9, 13 and 20: "Xaa" = any amino
      acid

<400> SEQUENCE: 5

Met Gln Ser Leu Pro Glu Ile Thr Xaa Leu Lys Ile Xaa Glu Lys Ala
  1               5                  10                  15

Ala Asp Tyr Xaa Asp Ile
                 20

<210> SEQ ID NO 6
<211> LENGTH: 6
<212> TYPE: PRT
<213> ORGANISM: Deinococcus radiophilus
```

-continued

<400> SEQUENCE: 6

Met Glu Leu Cys His Lys
 1               5

<210> SEQ ID NO 7
<211> LENGTH: 6
<212> TYPE: PRT
<213> ORGANISM: Deinococcus radiophilus

<400> SEQUENCE: 7

Glu Lys Ala Ala Asp Tyr
 1               5

<210> SEQ ID NO 8
<211> LENGTH: 18
<212> TYPE: DNA
<213> ORGANISM: Deinococcus radiophilus

<400> SEQUENCE: 8
atggarytnt gycayaar                                                    18

<210> SEQ ID NO 9
<211> LENGTH: 17
<212> TYPE: DNA
<213> ORGANISM: Deinococcus radiophilus

<400> SEQUENCE: 9
tartcngcng cyttytc                                                     17

<210> SEQ ID NO 10
<211> LENGTH: 20
<212> TYPE: DNA
<213> ORGANISM: Deinococcus radiophilus

<400> SEQUENCE: 10
cagcttggaa gagttcacag                                                  20

<210> SEQ ID NO 11
<211> LENGTH: 20
<212> TYPE: DNA
<213> ORGANISM: Deinococcus radiophilus

<400> SEQUENCE: 11
cccctgtagt catagttgca                                                  20

<210> SEQ ID NO 12
<211> LENGTH: 16
<212> TYPE: DNA
<213> ORGANISM: Deinococcus radiophilus

<400> SEQUENCE: 12
attctcttcg gtgacc                                                      16

<210> SEQ ID NO 13
<211> LENGTH: 18
<212> TYPE: DNA
<213> ORGANISM: Deinococcus radiophilus

<400> SEQUENCE: 13
tcgaggtgca tagtacaa                                                    18

<210> SEQ ID NO 14

```
<210> SEQ ID NO 14
<211> LENGTH: 20
<212> TYPE: DNA
<213> ORGANISM: Deinococcus radiophilus

<400> SEQUENCE: 14
tagggccaac tattcgcgga                                              20

<210> SEQ ID NO 15
<211> LENGTH: 21
<212> TYPE: DNA
<213> ORGANISM: Deinococcus radiophilus

<400> SEQUENCE: 15
tcaaagcctg aaaggcatct c                                            21

<210> SEQ ID NO 16
<211> LENGTH: 46
<212> TYPE: DNA
<213> ORGANISM: Deinococcus radiophilus

<400> SEQUENCE: 16
aaaactgcag ataaggaggt gatcgtatga cgaatgtgga acaagt                 46

<210> SEQ ID NO 17
<211> LENGTH: 39
<212> TYPE: DNA
<213> ORGANISM: Deinococcus radiophilus

<400> SEQUENCE: 17
cgcggatccc actgtgtgct atagctctgc ttcatgtgc                         39

<210> SEQ ID NO 18
<211> LENGTH: 31
<212> TYPE: DNA
<213> ORGANISM: Deinococcus radiophilus

<400> SEQUENCE: 18
ggaattccat atggagttgt gccacaagac t                                 31

<210> SEQ ID NO 19
<211> LENGTH: 29
<212> TYPE: DNA
<213> ORGANISM: Deinococcus radiophilus

<400> SEQUENCE: 19
aaaatctcga gctatagcat ttttacgcg                                    29

<210> SEQ ID NO 20
<211> LENGTH: 3604
<212> TYPE: DNA
<213> ORGANISM: Deinococcus radiophilus

<400> SEQUENCE: 20
gacgaaaggg cctcgtgata cgcctatttt tataggttaa tgtcatgata ataatggttt    60
cttagacgtc aggtggcact tttcggggaa atgtgcgcgg aaccccctatt tgtttatttt   120 tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt tgccttcct gttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
```

-continued

```
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acggggggtt   1560 cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 gggggcggag cctatggaaa aacgccagca acgcggcctt tttacggttc ctggccttt   1860 gctggccttt tgctcacatg gcgctcactg cccgctttcc agtcgggaaa cctgtcgtgc   1920
cagctgcatt aatgaatcgg ccaacgcgcg gggagaggcg gtttgcgtat gggcgccag   1980 ggtggttttt cttttcacca gtgagacggg caacagctga ttgcccttca ccgcctggcc   2040
ctgagagagt tgcagcaagc ggtccacgct ggtttgcccc agcaggcgaa aatcctgttt   2100
gatggtggtt aacggcggga tataacatga gctgtcttcg gtatcgtcgt atcccactac   2160
cgagatatcc gcaccaacgc gcagcccgga ctcggtaatg gcgcgcattg cgcccagcgc   2220
catctgatcg ttggcaacca gcatcgcagt gggaacgatg ccctcattca gcatttgcat   2280
ggtttgttga aaaccggaca tggcactcca gtcgccttcc cgttccgcta tcggctgaat   2340
ttgattgcga gtgagatatt tatgccagcc agccagacgc agacgcgccg agacagaact   2400
taatgggccc gctaacagcg cgatttgctg gtgacccaat gcgaccagat gctccacgcc   2460
cagtcgcgta ccgtcttcat gggagaaaat aatactgttg atgggtgtct ggtcagagac   2520
atcaagaaat aacgccggaa cattagtgca ggcagcttcc acagcaatgg catcctggtc   2580
atccagcgga tagttaatga tcagcccact gacgcgttgc gcgagaagat tgtgcaccgc   2640
cgctttacag gcttcgacgc cgcttcgttc taccatcgac accaccacgc tggcacccag   2700
ttgatcggcg cgagatttaa tcgccgcgac aatttgcgac ggcgcgtgca gggccagact   2760
```

-continued

```
ggaggtggca acgccaatca gcaacgactg tttgcccgcc agttgttgtg ccacgcggtt    2820
gggaatgtaa ttcagctccg ccatcgccgc ttccactttt tcccgcgttt tcgcagaaac    2880
gtggctggcc tggttcacca cgcgggaaac ggtctgataa gagacaccgg catactctgc    2940
gacatcgtat aacgttactg gtttcacatt caccaccctg aattgactct cttccgggcg    3000
ctatcatgcc ataccgcgaa aggttttgcg ccattcgatg gtgtcagcgt gagttagctc    3060
actcattagg cacccaggc tttacacttt atgcttccgg ctcgtataat gtgtggaatc     3120
acacaggaaa cagctatgac catgattacg ccaagcttgc atgcctgcag gtcgactcta    3180
gaggatcccc gggtaccgag ctcgaattca ctggccgtcg ttttacaacg tcgtgactgg    3240
gaaaaccctg gcgttaccca acttaatcgc cttgcagcac atccccttt cgccagctgg     3300 cgtaatagcg aagaggcccg caccgatcgc ccttcccaac agttgcgcag cctgaatggc    3360
gaatggcgcc tgatgcggta ttttctcctt acgcatctgt gcggtatttc acaccgcata    3420
tggtgcactc tcagtacaat ctgctctgat gccgcatagt taagccagcc ccgacacccg    3480
ccaacacccg ctgacgcgcc ctgacgggct tgtctgctcc cggcatccgc ttacagacaa    3540
gctgtgaccg tctccgggag ctgcatgtgt cagaggtttt caccgtcatc accgaaacgc    3600
gcga                                                                 3604

<210> SEQ ID NO 21
<211> LENGTH: 95
<212> TYPE: DNA
<213> ORGANISM: Deinococcus radiophilus

<400> SEQUENCE: 21
accccaggca ggggaccatt tacactttat gcttccggct cgtatgttgt gtggaattgt     60
gagcggataa caatttcaca caggaaacag ctatg                                95
```